(12) United States Patent
Klare et al.

(10) Patent No.: US 12,263,059 B2
(45) Date of Patent: Apr. 1, 2025

(54) ADAPTATION SYSTEM FOR ORAL APPLIANCE

(71) Applicant: PRO3DURE MEDICAL GMBH, Iserlohn (DE)

(72) Inventors: Martin Klare, Dortmund (DE); Konrad Hofmann, Thüngersheim (DE)

(73) Assignee: PRO3DURE MEDICAL GMBH, Iserlohn (DE)

( * ) Notice: Subject to any disclaimer, the term of this patent is extended or adjusted under 35 U.S.C. 154(b) by 595 days.

(21) Appl. No.: 17/438,430

(22) PCT Filed: Mar. 12, 2020

(86) PCT No.: PCT/EP2020/056740
§ 371 (c)(1),
(2) Date: Sep. 12, 2021

(87) PCT Pub. No.: WO2020/182968
PCT Pub. Date: Sep. 17, 2020

(65) Prior Publication Data
US 2022/0142746 A1    May 12, 2022

(30) Foreign Application Priority Data

Mar. 12, 2019 (EP) ..................................... 19162285
Apr. 16, 2019 (EP) ..................................... 19169667

(51) Int. Cl.
*A61B 5/00* (2006.01)
*A61B 5/021* (2006.01)
(Continued)

(52) U.S. Cl.
CPC .............. *A61C 7/36* (2013.01); *A61B 5/4542* (2013.01); *A61B 5/4818* (2013.01);
(Continued)

(58) Field of Classification Search
CPC .... A61C 7/36; A61C 7/08; A61C 7/00; A61B 5/4542; A61B 5/4818; A61B 5/4836;
(Continued)

(56) References Cited

U.S. PATENT DOCUMENTS 6,273,859 B1 * 8/2001 Remmers ................ A61F 5/566
607/42
6,613,001 B1 * 9/2003 Dworkin .................. A61C 7/00
600/590

(Continued)

*Primary Examiner* — Heidi M Eide
*Assistant Examiner* — Lina Faraj
(74) *Attorney, Agent, or Firm* — JMB Davis Ben-David

(57) ABSTRACT

The invention relates to an adaptation system (500), comprising a mouthpiece (10), configured to be positioned in a mouth of a person, and an external sensing device (20). The external sensing device (20) is configured to be positioned at the person, wherein the external sensing device (20) comprises at least one sensor (22) configured to sense at least one measurable quantity when the mouthpiece (10) is positioned in the person's mouth and the external sensing device (20) is positioned at the person. Further, the adaptation system (500) comprises an analysis device (30) configured to determine a compliance of the adaptation system and/or to determine an orientation of an upper jaw (100) and a lower jaw (200) to each other derived from the at least one sensed measurable quantity.

20 Claims, 3 Drawing Sheets

Figure 1:
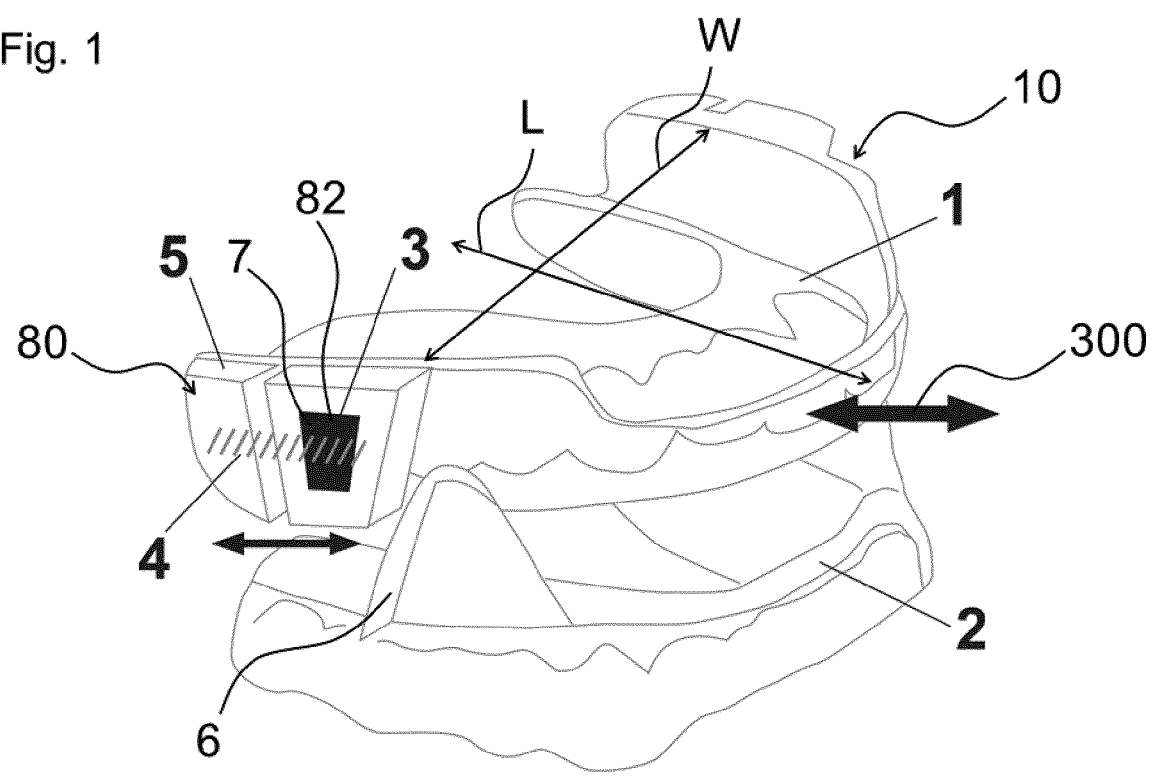

(51) Int. Cl.
  *A61B 5/024* (2006.01)
  *A61B 5/1455* (2006.01)
  *A61B 5/22* (2006.01)
  *A61B 7/00* (2006.01)
  *A61C 7/08* (2006.01)
  *A61C 7/36* (2006.01)
  *A61F 5/56* (2006.01)

(52) U.S. Cl.
  CPC .............. *A61B 5/4836* (2013.01); *A61C 7/08* (2013.01); *A61F 5/566* (2013.01); *A61B 5/021* (2013.01); *A61B 5/02438* (2013.01); *A61B 5/14551* (2013.01); *A61B 5/228* (2013.01); *A61B 5/6802* (2013.01); *A61B 7/003* (2013.01); *A61B 2560/0276* (2013.01)

(58) Field of Classification Search
  CPC . A61B 5/021; A61B 5/02438; A61B 5/14551; A61B 5/228; A61B 5/6802; A61B 7/003; A61B 2560/0276; A61F 5/566; A61F 5/56; A61F 2005/563
  See application file for complete search history.

(56) References Cited

U.S. PATENT DOCUMENTS

| | | | |
|---|---|---|---|
| 2006/0166157 A1* | 7/2006 | Rahman | A61B 5/4833 433/6 |
| 2011/0232652 A1* | 9/2011 | Levendowski | A61F 5/566 128/848 |
| 2011/0295083 A1* | 12/2011 | Doelling | A61B 5/11 600/407 |
| 2013/0140289 A1* | 6/2013 | Baratier | A61C 7/36 433/25 |
| 2014/0114146 A1* | 4/2014 | Hanewinkel | A61B 5/394 600/301 |
| 2014/0323839 A1* | 10/2014 | McCreery | A61B 5/4552 600/407 |
| 2015/0150501 A1 | 6/2015 | George | |
| 2016/0199215 A1 | 7/2016 | Kopelman | |
| 2016/0199216 A1* | 7/2016 | Cam | A61F 5/566 128/848 |
| 2018/0000565 A1* | 1/2018 | Shanjani | A61C 19/04 |
| 2018/0078403 A1* | 3/2018 | Remmers | G01N 33/48 |

* cited by examiner

ADAPTATION SYSTEM FOR ORAL APPLIANCE

CROSS-REFERENCE TO RELATED APPLICATIONS

This is the U.S. National Stage of International Patent Application No. PCT/EP2020/056740 filed on Mar. 12, 2020, which claims priority to European Patent Application No. 19/162,285.1 filed on Mar. 12, 2019, and European Patent Application No. 19/169,667.3 filed on Apr. 16, 2019.

A sleep disorder is a medical disorder of the sleep pattern of a person. A group of sleep disorders is associated to the breathing of the person, including snoring, sleep hypopnea, or sleep apnoea. They can interrupt the sleep of the person and can increase the risk of severe diseases such as a heart failure, a heart attack or a stroke.

Snoring can be a precursor of a sleep apnoea. A person suffering from sleep hypopnea has a decreased respiratory flow, for instance due to a low respiratory rate or due to a shallow breathing. A person with sleep apnoea can even show pauses in breathing during sleep still increasing the risk of a heart failure, a heart attack or a stroke.

The breathing of a person can be affected by the sleeping position, in particular by a disadvantageous position of the head. A disadvantageous head position can lead to a narrowing of the respiratory system, thus impairing breathing. Also, the weight of the person affects the airflow and hence the breathing. In particular, fat deposit at the neck can impede breathing. Further, the state of the soft palate can have an impact on breathing. If the soft palate is in a relaxed mode, it can at least partially block the airway leading to an abnormal airflow.

For a person suffering from a sleep disorder it is important to detect indicators of a sleep disorder such as a low respiratory rate or pauses in breathing, and even more importantly to take precautions to prevent the occurrence or to prevent continuation of those indicators. For this purpose, devices are known for the observation of the breathing of the person during sleep, the observation of an indicator of a sleep disorder and/or the sleep of the person in general.

With respect to a sleep disorder associated to breathing, an oral appliance is known that keep the airways of the person mechanically open, such as Somnomed products. A narrowing of the throat is reduced. This way, such an oral appliance can facilitate breathing and can reduce the implications of a breathing associated sleep disorder.

An oral appliance can affect the anatomic state of the oral cavity of a person. For instance, a protrusion of the lower jaw can affect the position of the soft palate that can have an impact on breathing. If the soft palate is in a relaxed mode, it can at least partially block the airway leading to an abnormal airflow. A protrusion of the lower jaw can prevent the relaxation of the soft palate such that breathing of the person can be improved.

Over time, the effect of such an oral appliance on the breathing can decrease, for instance if the oral appliance does not fit properly anymore. For instance, the fitting of the oral appliance can decline if the body of the person changes, e.g. if the person gains or loses weight. It is also possible that the fitting of the oral appliance declines due to intensive use or because of its age.

State-of-the-art oral appliance can comprise a device configured to detect whether the device is in use or not (US 2015/01 50 501 A1). However, the oral appliance does not detect the compliance of the oral appliance, in particular whether the oral appliance works properly.

Therefore, a device is of interest that facilitates breathing wherein the device is furthermore configured such that it can be checked whether the device performs its function properly and that can improve its functioning.

This is solved by the system described in claim 1. Embodiments of the aspects of the present invention are stated in the corresponding sub claims and are described below.

A first aspect of the invention is related to an adaptation system, which comprises a mouthpiece, configured to be positioned in a mouth of a person, and an external sensing device, configured to be positioned at the person. The external sensing device comprises at least one sensor configured to sense at least one measurable quantity when the mouthpiece is positioned in the person's mouth and the external sensing device is positioned at the person. Further, the adaptation system comprises an analysis device configured to determine a compliance of the adaptation system and/or to determine an orientation of an upper jaw and a lower jaw to each other derived from the at least one sensed measurable quantity.

To determine the compliance of the adaptation system particularly means that based on the at least one sensed measurable quantity, the adaptation system can detect whether it works properly. The system can also detect an improper functioning.

Advantageously, the adaptation system check whether it is in use or not but and/or determines whether it functions properly.

When the system detects an improper functioning, the system can adapt at least one property of the system in order to increase the compliance.

In an embodiment the orientation of the person's jaws to each other can be determined based on the at least one sensed measurable quantity. In an embodiment, the system determines whether the orientation of the jaws to each other provides a proper functioning, i.e. a good compliance, of the system. In other words it is checked whether the jaws are positioned to each other in a proper position and in a defective position. In an embodiment, an absolute position of the lower jaw to the upper jaw can be determined.

The orientation of an upper jaw and a lower jaw to each other can be described by the position of the mandibular front teeth in relation to the maxillary front teeth. A distance in the superior-inferior direction is also referred to as vertical distance. A distance in the anterior-posterior direction is also referred to as horizontal distance. A distance in the left-right direction is also referred to as lateral distance.

The position of the upper jaw and the lower jaw to each other can have an impact on the opening of the mouth of the person and can determine the anatomic state of the oral cavity, in particular the position of the soft palate.

The at least one sensor can be in direct contact with the person, in particular in direct contact with the skin of the person. In an alternative embodiment, the at least one sensor is positioned distant to the person. This particularly means that the at least one sensor can be positioned such that it does not directly contact the skin of the person at that the external sensing device is positioned.

In an embodiment, the at least one sensor is positioned outside the oral cavity.

Alternatively, the at least one sensor can be positioned in the oral cavity. In an embodiment, the mouthpiece can comprise the at least one sensor.

In an embodiment, the external sensing device comprises a plurality of sensors. In an embodiment, each sensor of the plurality of sensors is configured to sense a specific measurable quantity. In particular, in an embodiment, each measurable quantity is sensed by a different sensor of the plurality of sensors.

Alternatively, the at least one sensor can be configured to sense a plurality of measurable quantities.

A sensed measurable quantity and/or a plurality of sensed measurable quantities can provide sensed information. This can also be referred to as sensed data.

The analysis device can be configured to derive the orientation of the upper jaw in relation to the lower jaw directly based on one sensed measurable quantity. In another embodiment, the analysis device is configured to derive the orientation of the upper jaw in relation to the lower jaw based on a plurality of sensed measurable quantities.

In an embodiment of the invention, the external sensing device comprises the analysis device.

The external sensing device can directly analyse the sensed data, i.e. the sensed measurable quantity. Advantageously, no additional devices for the analyses of the data are necessary. Therefore, the adaptation system is small and easy to transport.

In an embodiment, the external sensing device and/or the analysis device is configured to perform a pre-processing of the sensed data, wherein pre-processed data is generated. In an embodiment, the external sensing device and/or the analysis device is configured to transmit the sensed data and/or the pre-processed data for storage. The external sensing device and/or the analysis device can be configured to transmit the sensed data and/or the pre-processed data for a further analysis.

According to an embodiment, data is transmitted to a cloud storage service. Via the cloud storage service an attending physician can easily access the sensed data and/or the pre-processed data.

In an embodiment, the external sensing device is configured to store the sensed or pre-processed data.

An embodiment is characterised in that the external sensing device is at least one of: a clothing comprising an intelligent textile, a breathing belt, a wearable computer, and in particular an ear piece, in particular a hearable.

A clothing comprising an intelligent textile can be an electronic textile, also known as smart clothing or smart textile.

In an embodiment, the wearable computer is a smart watch. In an alternative embodiment, the wearable computer is a fitness tracker. A smart watch as well as a fitness tracker are small. Therefore, one of these external sensing devices is advantageously easy to transport. Additionally, due to its small size, the smart watch and/or the fitness tracker can be in direct contact with the person without or at least without substantially dictating a specific sleeping position of the person.

In an embodiment, the wearable computer is a smartphone. In an embodiment, the wearable computer is a tablet computer.

According to the invention, the wearable computer can be a heart rate monitoring device.

According to the invention, the external sensing device can be an ear piece. In particular, it can be a hearable. A hearable can also be referred to as smart headphone. A hearable can be an in-ear-device. It can comprise an analysis device and/or a storage device.

An ear piece is small such that it is easy to transport. Advantageously, it does not or at least not substantially affect the sleeping position of the person wearing the ear piece. Therefore, the adaptation phase to become familiar with the external sensing device can be short.

According to an embodiment, the mouthpiece is adaptable to modify the orientation of the upper jaw and the lower jaw to each other based on the at least one sensed measurable quantity.

In an embodiment, the mouthpiece is adaptable to modify the vertical distance. Alternatively, the horizontal distance can be modified by adapting the mouthpiece. In an embodiment, the mouthpiece is adaptable to modify the lateral distance.

In an embodiment, the system is configured to modify the orientation of the upper jaw in relation to the lower jaw when the at least one sensed measurable quantity indicates an abnormal breathing. In particular, the mouthpiece can be configured to provide a protrusion of the lower jaw. The protrusion can prevent the relaxation of the soft palate improving the breathing of the person.

In an embodiment, the mouthpiece comprises a distractor, wherein the distractor is configured to modulate at least one property of the mouthpiece to modify the orientation of the upper jaw and the lower jaw to each other.

According to an embodiment, the system comprises a modulation device through which the distractor is accessible to modify the orientation of the upper jaw and the lower jaw to each other, wherein in particular the modulation device comprises a micromotor or, wherein the distractor is manually adjustable.

In an embodiment, the modulation device comprises a micromotor. The micromotor can be accessible by an external modulation control device. The micromotor can automatically modulate at least one property of the mouthpiece.

In an embodiment, the distractor is manually adjustable.

In an embodiment, the system comprises a feedback device configured to determine a modification of the orientation of the upper jaw and the lower jaw to each other from the modulation of at least one property of the mouthpiece by the distractor.

In an embodiment, the system is configured to detect whether the system, in particular the mouthpiece, works properly. In the context of the application, the system is considered to work properly, when a modification of the mouthpiece leads to improved breathing of the person, when the system has detected abnormal breathing before the modification, Improved breathing can be indicated by at least one property including decreased snoring, increased blood oxygen saturation.

In other words, this means that the system can be configured to detect a compliance of the system. The system can be configured to analyse whether it functions properly, in particular whether it improves breathing.

In an embodiment, the analysis device is configured to detect the compliance. In an embodiment, the feedback device is configured to detect the compliance.

The feedback device can be configured to detect whether an adjustment of the mouthpiece by modulation of one of its property by the distractor modifies the orientation of the jaws to each other appropriately. In particular, in an embodiment, the feedback device is configured to detect whether an adjustment of the mouthpiece leads to an appropriate modification of the breathing of the person, in particular whether the airflow is improved.

The feedback device can be configured to determine a modification of the orientation of the upper jaw and the lower jaw to each other over time, and in particular the modification of the breathing over time.

In an embodiment, the system is configured such that the orientation of the upper jaw and the lower jaw to each other is modified until the feedback device detects a predefined orientation of the upper jaw and the lower jaw, in particular until the feedback device detects a predefined breathing property of the person. A breathing property can be one of a breathing sound, a snoring sound, a respiratory rate, a blood oxygen saturation, and a breathing frequency.

An embodiment is characterised in that the at least one property of the mouthpiece is one of a width of the mouthpiece, a length of the mouthpiece, and a height of at least a section of the mouthpiece.

In an embodiment, the mouthpiece comprises an upper oral splint related to the upper jaw of the person and/or a lower oral splint related to the lower jaw of the person.

The upper oral splint and or the lower oral splint can particularly be personalised for the respective person.

According to an embodiment, the at least one property of the mouthpiece is an angle between the upper oral splint and the lower oral splint, and/or an offset between the upper oral splint and the lower oral splint.

In an embodiment, the modification of an angle between the upper oral splint leads to a modification of the opening of the oral cavity.

A modification of at least one property of the mouthpiece can mediate a modification of the anatomic properties of the oral cavity such that the airflow is improved. The modification of at least one property of the mouthpiece can counteract a narrowing of the respiratory system, i.e. counteract the narrowing of the airways. This means that modification of at least one property of the mouthpiece can improve breathing.

In an embodiment, the offset between the upper oral splint and the lower oral splint is the respective offset in relation to the horizontal direction. A modification of this offset can provide a protrusion of the lower jaw. A protrusion of the lower jaw can prevent the relaxation of the soft palate. A relaxed soft palate can partially block the airway, impairing breathing. When the relaxation is prevented, breathing can be improved. For instance, the blood oxygen saturation can increase.

In an embodiment, the system comprises a prediction device which is configured to evaluate a template dataset based on the at least one measurable quantity sensed by the at least one sensor, wherein the template dataset characterises a template of an optimised mouthpiece with modified orientation of the upper jaw and the lower jaw to each other.

In an embodiment, the system is configured to transmit the template dataset to a 3D printer, in particular to a digital light processing printer.

In an embodiment, an optimised mouthpiece can be printed by a 3D printer, based on the template dataset.

In an alternative embodiment, based on the template dataset a positive of a dental arch related to the upper jaw and/or a positive of a dental arch related to the lower jaw can be printed by the 3D printer. The 3D printed dental arch can serve as a model on that an optimised mouthpiece is generated.

According to the invention, the optimised mouthpiece can be generated based on a previous mouthpiece, in particular on a previous mouthpiece with modified orientation of the upper and the lower splint.

According to an embodiment, that the at least one sensor is one of: a sound sensor, a temperature sensor, an inclination sensor, a heart rate senor, a blood pressure sensor, a blood oxygen sensor, a muscle tension sensor.

In an embodiment, the at least one sensor can sense a vital function of the person.

In an embodiment, the sound sensor is a sensor for sensing breathing sound. In an alternative embodiment, the sound sensor senses snoring sound. Alternatively, the sound sensor can sense a sound of teeth grinding.

In an embodiment, the muscle tension sensor senses the tension of a jaw muscle. By detecting the tension of a jaw muscle, a clenching of the jaws and/or grinding of teeth can be sensed.

An inclination sensor can sense the position of the person during sleep. In an embodiment, the inclination sensor detects the kind and/or number of positional changes of a person.

According to an embodiment, the inclination sensor is configured to detect the position of the head. The sensor can detect the kind and/or number of positional changes of the head.

In an embodiment, the blood oxygen sensor measures the oxygen saturation in the blood of the person. In an embodiment, the blood oxygen saturation can be sensed by a pulse oximeter. According to an embodiment, an earpiece comprises the pulse oximeter.

According to an embodiment, the system is configured to measure the at least one sensed measurable quantity continuously over time.

In an embodiment, the system detects a vital function of the person continuously over time.

Due to a continuous measurement, deviations from reference values can be immediately be detected. The system can immediately react to the deviation, in particular by modifying the orientation of the upper and the lower jaw to each other.

An embodiment is characterised in that the system is configured to measure the at least one measurable quantity at a plurality of predefined time points, in particular at a plurality of successive equally spaced time points.

In an embodiment, the at least one measurable quantity is sensed every minute. In an alternative embodiment, the at least one measurable quantity is sensed every 2 minutes. Alternatively, the at least one measurable quantity is sensed every 5 minutes.

In an embodiment, the blood oxygen saturation is measured at predefined time points, in particular every 15 minutes, in particular every 10 minutes, in particular every 5 minutes, in particular every 2 minutes. Each measured data point (i.e. the blood oxygen saturation measured at the respective time point) can be compared to a predefined reference value. In an embodiment, a measured data point is compared to at least one previously measured data point, i.e. at least one measured data point detected at a previous time point.

A decrease in the blood oxygen saturation can indicate an abnormal airflow. It can indicate that the airways are narrowed.

In an embodiment, at least one property of the mouthpiece is modified to improve the airflow (improve breathing) by opening the airways to counteract the decreased blood oxygen saturation. This means, the at least one property of the mouthpiece can be modified in order to increase blood oxygen saturation.

In an embodiment, the system is configured to analyse the at least one measurable quantity in real-time.

In an embodiment, the analysis device is configured to analyse the at least one measurable quantity in real-time.

In particular this means that a data point measured at a particular time point can be analysed during or directly after its measurement.

When the sensed data is analysed in real-time, changes that can have a negative impact on the breathing and/or the sleep can be detected in real-time. Hence, the system can counteract the negative impact in real-time, in particular the system can modify at least one property of the mouthpiece that such that the anatomic properties of the oral cavity can advantageously be changed. In an embodiment, the orientation of the upper jaw and the lower jaw to each other can be modified in real-time.

In an embodiment, the mouthpiece can be modified in real-time, when a sensor senses increased snoring. In particular, the mouthpiece can be modified such that the protrusion of the lower jaw is provided and/or intensified.

In an embodiment, at least one property of the mouthpiece can be changed in real-time when a sensor, in particular a pulse oximeter, senses a decrease in the blood oxygen saturation.

An advantage of analysing the data in real time is that deviations in the sensed data and/or changes in the airflow are immediately determined. The system, in particular the mouthpiece, can be adapted in real time to counteract, in particular to increase the compliance of the system.

In an embodiment, the system comprises an alert device configured to compare at least one measurable quantity with a predefined reference value of the respective at least one measurable quantity.

According to an embodiment, the alert device is configured to give an alert to the person, when the at least one measurable quantity deviates from the predefined reference value of the respective at least one measurable quantity by a predefined deviation factor.

In particular, the system is configured to compare at least one measurable quantity with a predefined respective reference value in real-time. Hence, a deviation of a particular measurable quantity from the respective predefined reference value can be detected in real-time.

According to the invention, at least one property of the mouthpiece is modified, in particular the mouthpiece is adjusted, when at least one biometric measurable quantity deviates from its respective predefined reference value. A biometric measure can be one of a blood oxygen saturation, a blood pressure, a pulse, a temperature, a muscle tension, a jaw muscle tension, a snoring sound and, a breathing sound.

In an embodiment, the mouthpiece is adjusted when the sensed measurable quantity deviates from the respective predefined reference value. In an embodiment, the mouthpiece is adjusted when snoring sound is increased. In an embodiment, the mouthpiece is adjusted when the blood oxygen saturation is below a respective reference value.

The system can be configured to detect whether the deviation from the respective predefined reference value decreases when the at least one property of the mouthpiece. In an embodiment, the system is configured to analyse whether the blood oxygen saturation increases after the modification of the mouthpiece.

In an embodiment, the alert device gives an alert to the person when the sensed measurable quantity strongly deviates from the respective predefined reference value.

In an embodiment, an alert is given to the person when an abnormal breathing pause is sensed by the system.

In an embodiment, the system is configured to determine a sleep disorder, wherein the sleep disorder is in particular snoring, sleep hypopnea, or sleep apnoea.

Figure 2:
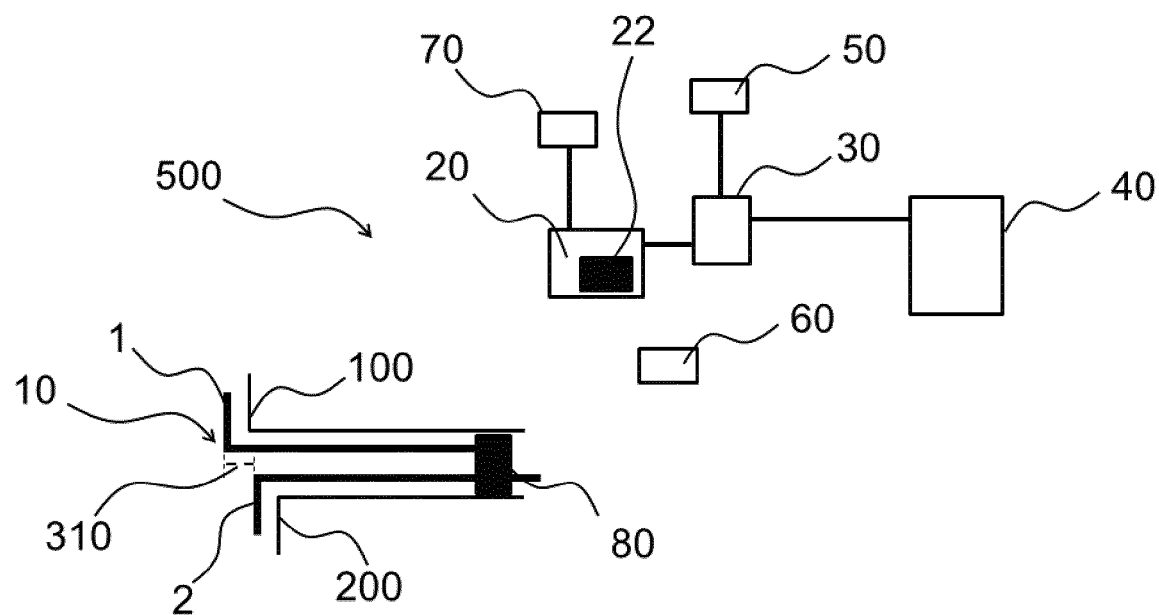
Figure 3:
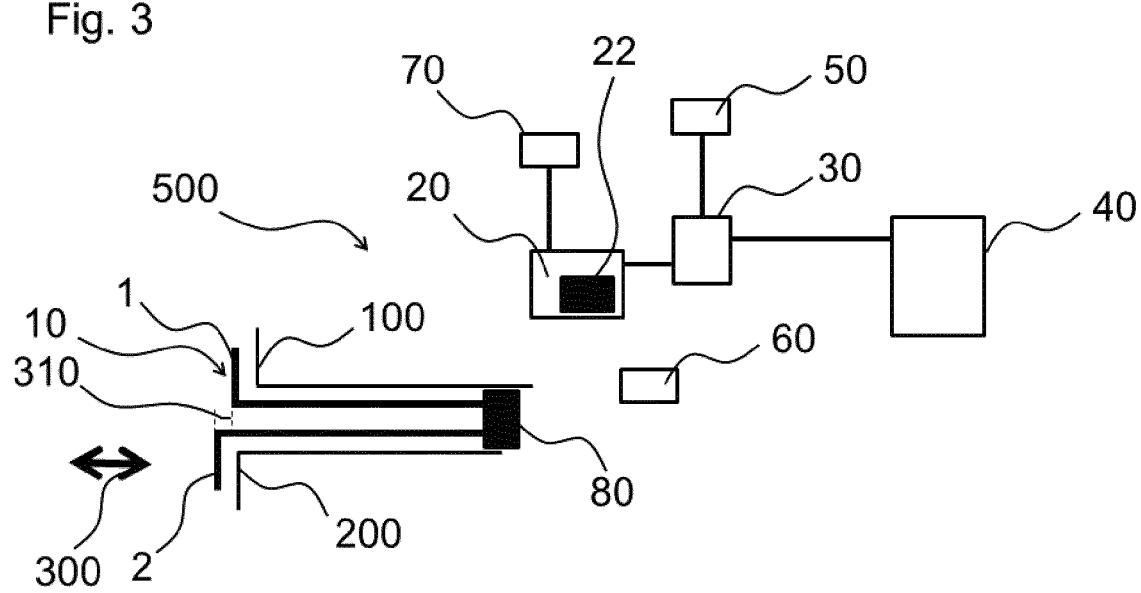
Figure 4:
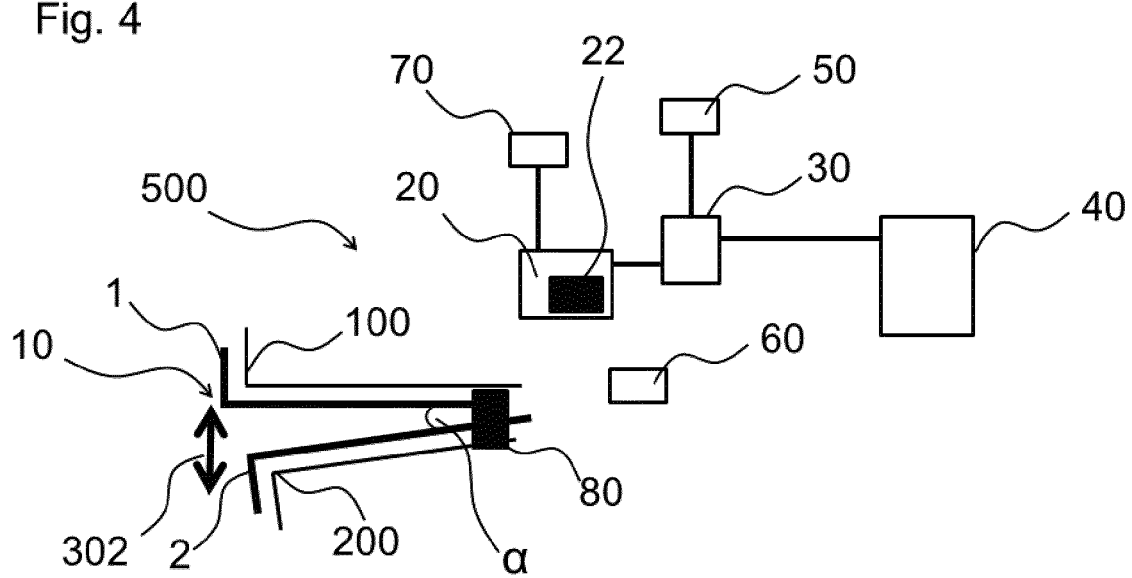

In the following, further features, advantages and embodiments of the present invention are explained with reference to the Figures, wherein FIG. 1 shows a schematic perspective representation of a mouthpiece, FIG. 2 shows a scheme of the system, wherein the upper jaw and the lower jaw are in an initial orientation, and FIG. 3 shows a scheme of the system, wherein the upper jaw and the lower jaw are in a horizontally modified orientation, and FIG. 4 shows a scheme of the system, wherein the upper jaw and the lower jaw are in a vertically modified orientation.

FIG. 1 illustrates a mouthpiece 10 comprising an upper oral splint 1 and a lower oral splint 2. In particular, the upper oral splint 1 and a lower oral splint 2 are individually personalised for the respective person. In the shown embodiment, the mouthpiece 10 is configured such that the position of the lower oral splint 2 can be modified such that a horizontal distance 300 can be modified when the mouthpiece 10 is positioned in the mouth of a person.

The lower oral splint 2 can comprise a driving element 6.

The mouthpiece 10 can comprise a distractor 80. In an embodiment, the distractor 80 comprises a spindle 4, a motor 3, in particular a micro-motor 3, a holding element 5 and a movement element 7. The spindle 4 can be movably coupled with the holding element 5 and the motor 3. By means of the motor 3 and the spindle 4, a distance between the holding element 5 and the movement element 7 can be modified.

The movement element 7 can push against the driving element 6. In an embodiment this pushing results in a modification of the position of the lower oral splint 2.

FIG. 2, FIG. 3 and FIG. 4 show a system 500 comprising a mouthpiece 10 comprising an upper oral splint 1 and a lower oral splint 2, wherein the upper oral splint 1 is positioned at the upper jaw 100 and the lower oral splint 2 is positioned at the lower jaw 200.

FIG. 2 shows the system 500 in an initial state. The term "initial state" means that in this state the orientation of the jaws 100, 200 is not modified by the mouthpiece 10.

FIG. 3 and FIG. 4 each show the system 500 in an adjusted state. The term "adjusted state" means that in this state the orientation of the lower jaw 200 in relation to the upper jaw 100 is modified by the mouthpiece 10.

FIG. 3 shows an adjusted state in that the orientation of the lower jaw 200 can be modified in the horizontal direction 300. In particular, the mouthpiece 10 can modify the orientation of the upper jaw 100 and the lower jaw 200 to each other such that the lower jaw 200 can perform a protrusion.

FIG. 4 shows an adjusted state in that the orientation of the lower jaw 200 with respect to the upper jaw 100 can be modified in the vertical direction 302.

The mouthpiece 10 can comprise a distractor 80 that can be configured to modulate at least one property of the mouthpiece 10, for instance the orientation of the upper oral splint 1 and the lower oral splint 2 to each other, to modify the orientation of the upper jaw 100 and the lower jaw 200 to each other.

In an embodiment, the distractor 80 is configured to modulate the offset 310 between the upper oral splint 1 and the lower oral splint 2, in particular the offset 310 along the horizontal direction 300 (FIG. 3).

In an alternative embodiment, the distractor 80 is configured to modulate an angle α between the upper oral splint 1 and the lower oral splint 2. By modulating the angle α, the distractor 80 can modulate the orientation of the upper oral splint 1 and the lower oral splint 2 in the vertical direction 302 (FIG. 4).

In an embodiment, the system 500 comprises an external sensing device 20. The external sensing device 20 can comprise a sensor 22 (FIG. 2, FIG. 3, FIG. 4).

The external sensing device 20, in particular the sensor 22, can be configured to sense, i.e. detect, at least one measurable quantity when the external sensing device 20 is positioned at the person. The sensed at least one measurable quantity is also referred to as sensed data or sensed information.

In an embodiment, the system 500 comprises an analysis device 30 (FIG. 2, FIG. 3, FIG. 4). The analysis device 30 can be configured to derive the orientation of the upper jaw 100 and the lower jaw 200 to each other based on the sensed at least one measurable quantity. In an embodiment, the analysis device 30 determines the compliance of the system 500.

According to the invention, the system 500 can comprise a storage device 40 (FIG. 2, FIG. 3, FIG. 4). In an embodiment, the analysis device 30 can transmit the sensed data to the storage device 40. The storage device 40 can be configured to store the sensed data.

In an embodiment, the system 500 comprises an alert device 50. The alert device 50 can be coupled to the analysis device 30.

The system 500 can comprise a feedback device 60. The feedback device 60 can be configured to detect whether an adjustment of the mouthpiece 10, in particular the modification of the orientation of the upper and the lower splint 1, 2 to each other, modifies the orientation of the jaws 100, 200 to each other appropriately. In particular, the feedback device 60 can be configured to detect whether an adjustment of the mouthpiece 10 results in an appropriate modification of the breathing of the person. In an embodiment, the feedback device 60 detects the compliance of the system 500.

In an embodiment, the analysis device 30 comprises the feedback device 60. In an alternative embodiment, the feedback device 60 is connected to the analysis device 30 and/or to the external sensing device 20.

In an embodiment, the system 500 comprises a prediction device 70. The prediction device 70 can be configured to evaluate a template dataset based on the at least one measurable quantity sensed by the sensor 22.

The invention claimed is:

1. An adaptation system (500), comprising
   a mouthpiece (10), configured to be positioned in a mouth of a person,
   an external sensing device (20), configured to be positioned at the person,
   wherein the external sensing device (20) comprises at least one sensor (22) configured to sense at least one measurable quantity when the mouthpiece (10) is positioned in the person's mouth and the external sensing device (20) is positioned at the person,
   wherein
   the adaptation system (500) comprises an analysis device (30) configured to determine a compliance of the adaptation system and/or to determine an orientation of an upper jaw (100) and a lower jaw (200) to each other derived from the at least one sensed measurable quantity,
   characterised in that
   the system (500) comprises a prediction device (70) which is configured to evaluate a template dataset based on the at least one measurable quantity sensed by the at least one sensor (22), wherein the template dataset characterises a template of an optimised mouthpiece (10') with modified orientation of the upper jaw (100) and the lower jaw (200) to each other, wherein the system (500) is configured to transmit the template dataset to a 3D printer.

2. The system (500) according to claims 1, characterised in that the external sensing device (20) comprises the analysis device (30).

3. The system (500) according to claim 1, characterised in that the external sensing device (20) is at least one of: a clothing comprising an intelligent textile, a breathing belt, a wearable computer and a smart headphone.

4. The system (500) according to claim 3, wherein the external sensing device is a smart headphone and the smart headphone is an ear piece.

5. The system (500) according to claim 1, characterised in that the mouthpiece (10) is adaptable to modify the orientation of the upper jaw (100) and the lower jaw (200) to each other based on the at least one sensed measurable quantity.

6. The system (500) according to claim 1, characterised in that the mouthpiece (10) comprises a distractor (80), wherein the distractor (80) is configured to modulate at least one property of the mouthpiece (10) to modify the orientation of the upper jaw (100) and the lower jaw (200) to each other.

7. The system (500) according to claim 6, characterised in that the system (500) comprises a feedback device (60) configured to determine a modification of the orientation of the upper jaw (100) and the lower jaw (200) to each other from the modulation of at least one property of the mouthpiece (10) by the distractor (80).

8. The system (100) according to claim 6, characterised in that the at least one property of the mouthpiece (10) is one of:
   a width (W) of the mouthpiece (10),
   a length (L) of the mouthpiece (10), and
   a height of at least a section of the mouthpiece (10).

9. The system (500) according to claim 6, characterised in that the mouthpiece (10) comprises an upper oral splint (1) related to the upper jaw (100) of the person and/or a lower oral splint (2) related to the lower jaw (200) of the person.

10. The system according to claim 9, characterised in that the mouthpiece comprises an upper oral splint related to the upper jaw of the person and a lower oral splint related to the lower jaw of the person and the at least one property of the mouthpiece is an angle between the upper oral splint and the lower oral splint, and/or an offset between the upper oral splint and the lower oral splint.

11. The system (500) according to claim 1, characterised in that the mouthpiece (10) comprises an upper oral splint (1) related to the upper jaw (100) of the person and/or a lower oral splint (2) related to the lower jaw (200) of the person.

12. The system (500) according to claim 1, characterised in that the at least one sensor (22) is one of: a sound sensor, a temperature sensor, an inclination sensor, a heart rate senor, a blood pressure sensor, a blood oxygen sensor, a muscle tension sensor.

13. The system (500) according to claim 1, characterised in that the system (500) is configured to measure the at least one measurable quantity continuously over time, or in that the system (500) is configured to measure the at least one measurable quantity at a plurality of predefined time points.

14. The system (500) according to claim 1, characterised in that the system (500) is configured to analyse the at least one measurable quantity in real-time.

15. The system (500) according to claim 1, characterised in that the system (500) comprises an alert device (50)

configured to compare at least one measurable quantity with a predefined reference value of the respective at least one measurable quantity.

16. The system (500) according to claim 15, characterised in that the system (500) comprises the alert device (50) configured to give an alert to the person, when the at least one measurable quantity deviates from the predefined reference value of the respective at least one measurable quantity by a predefined deviation factor.

17. The system (500) according to claim 1, characterised in that the system (500) is configured to determine a sleep disorder.

18. The system (500) according to claim 1, characterised in that the mouthpiece (10) comprises a modulation device (82) through which a distractor (80) is accessible to modify the orientation of the upper jaw (100) and the lower jaw (200) to each other.

19. The system (500) according to claim 1, characterised in that the system (500) is configured to measure the at least one measurable quantity continuously over time, or in that the system (500) is configured to measure the at least one measurable quantity at a plurality of successive equally spaced time points.

20. The system (500) according to claim 1, characterised in that the system (500) is configured to determine a sleep disorder, wherein the sleep disorder is snoring, sleep hypopnoea, or sleep apnoea.

* * * * *